United States Patent
Razavi et al.

(10) Patent No.: US 10,751,119 B2
(45) Date of Patent: Aug. 25, 2020

(54) METHOD AND DEVICE FOR DETECTION OF ARRHYTHMIAS AND MYOCARDIAL INJURY

(71) Applicant: Texas Heart Institute, Houston, TX (US)

(72) Inventors: Mehdi Razavi, Houston, TX (US); Mohammad Madjid, Houston, TX (US); James T. Willerson, Houston, TX (US)

(73) Assignee: TEXAS HEART INSTITUTE, Houston, TX (US)

( * ) Notice: Subject to any disclaimer, the term of this patent is extended or adjusted under 35 U.S.C. 154(b) by 659 days.

(21) Appl. No.: 15/209,319

(22) Filed: Jul. 13, 2016

(65) Prior Publication Data
US 2017/0014182 A1  Jan. 19, 2017

Related U.S. Application Data

(60) Provisional application No. 62/192,819, filed on Jul. 15, 2015.

(51) Int. Cl.
*A61B 18/14* (2006.01)
*A61B 34/20* (2016.01)
(Continued)

(52) U.S. Cl.
CPC ........ *A61B 18/1492* (2013.01); *A61B 5/0036* (2018.08); *A61B 5/015* (2013.01);
(Continued)

(58) Field of Classification Search
CPC ..... A61B 5/015; A61B 5/0422; A61B 5/4836; A61B 5/6858; A61B 2018/00821;
(Continued)

(56) References Cited

U.S. PATENT DOCUMENTS

| 2003/0028114 A1* | 2/2003 | Casscells, III | A61B 5/0077 600/474 |
| 2007/0043298 A1* | 2/2007 | Plouf | A61B 5/0031 600/485 |

(Continued)

OTHER PUBLICATIONS

PCT International Preliminary Report on Patentability dated Jan. 25, 2018 for corresponding Application No. PCT/US2016/042068, 10 pages.

(Continued)

*Primary Examiner* — Eun Hwa Kim
*Assistant Examiner* — C. C. P.
(74) *Attorney, Agent, or Firm* — Jonathan Pierce; Pierre Campanac; Porter Hedges LLP

(57) ABSTRACT

Herein disclosed is a method of detecting and identifying the source of abnormal electrical currents in the heart to assist in ablating these currents, comprising the use of contact or non-contact temperature measurement devices. In an embodiment, source of abnormal electrical activity of the heart and its attached arteries and veins show different temperature patterns from normal segments. In an embodiment, the method further comprises analyzing the temperature of the chamber of interest, and determining regions of low or high temperature by extension metabolic activity. In an embodiment, the method comprises measuring myocardial temperature comprising placing an array of thermocouples imbedded on a basket in the cardiac chamber. In an embodiment, the thermocouples are placed in contact with the myocardial tissue.

24 Claims, 7 Drawing Sheets

(51) Int. Cl.
- *A61B 5/042* (2006.01)
- *A61B 5/00* (2006.01)
- *A61B 5/01* (2006.01)
- *A61B 18/00* (2006.01)
- *A61B 17/00* (2006.01)

(52) U.S. Cl.
CPC .......... *A61B 5/0422* (2013.01); *A61B 5/4836* (2013.01); *A61B 5/6858* (2013.01); *A61B 34/20* (2016.02); *A61B 2017/00221* (2013.01); *A61B 2017/00734* (2013.01); *A61B 2018/00267* (2013.01); *A61B 2018/00351* (2013.01); *A61B 2018/00577* (2013.01); *A61B 2018/00821* (2013.01); *A61B 2018/00827* (2013.01); *A61B 2018/00875* (2013.01); *A61B 2034/2074* (2016.02)

(58) Field of Classification Search
CPC ........... A61B 2018/00267; A61B 2018/00351; A61B 2018/00577; A61B 2018/00827; A61B 2018/00875; A61B 18/1492; A61B 34/20; A61B 2034/2074; A61B 2017/00221; A61B 2017/00734
See application file for complete search history.

(56) References Cited

U.S. PATENT DOCUMENTS

2009/0043223 A1* 2/2009 Zhang .................... A61B 5/015
600/549
2011/0144509 A1* 6/2011 Kahlert ................ A61B 5/0422
600/508
2013/0006139 A1* 1/2013 Tiano .................... A61B 5/015
600/549

OTHER PUBLICATIONS

Payam Safavi-Naeini et al., "Cryoballoon Pressure Waveform Change during Balloon Inflation is not a Reliable Predictor of Adequate Pulmonary Vein Occlusion", PACE, vol. 37, Dec. 2014, (p. 1702-1707).

Payam Safavi-Naeini et al., "Review: Focal Impulse and Rotor Modulation (FIRM) Ablation", vol. 14, Issue 6, Jun. 2014, (4 pages).

2014 AHA/ACC/HRS Guideline for the Management of Patients With Atrial Fibrillation: Executive Summary, Journal Of The American College Of Cardiology, vol. 64, No. 21, 2014, (35 pages).

Payam Safavi-Naeini et al., "A Review of the LARIAT Suture Delivery Device for Left Atrial Appendage Closure", The Journal of Tehran University Heart Center, Apr. 2015, (p. 69-73).

Michael H. Kim et al., "Estimation of Total Incremental Health Care Costs in Patients With Atrial Fibrillation in the United States", Circulation: Cardiovascular Quality and Outcomes Journal, May 2011, (p. 315-321).

Sanjiv M. Narayan et al., "Treatment of Atrial Fibrillation by the Ablation of Localized Sources", Journal Of The American College Of Cardiology vol. 60, No. 7, 2012, (p. 628-636).

Mohammad Madjid, MD, et al., "Intracoronary Thermography for Detection of High-Risk Vulnerable Plaques" Journal Of The American College of Cardiology vol. 47, No. 8 (pp. C80-C85).

International Search Report and Written Opinion dated Oct. 6, 2016 for Application No. PCT/US2016/042068 (15 pgs.).

* cited by examiner

METHOD AND DEVICE FOR DETECTION OF ARRHYTHMIAS AND MYOCARDIAL INJURY

CROSS-REFERENCE TO RELATED APPLICATIONS

This application claims the benefit under 35 U.S.C. § 119(e) of U.S. Provisional Patent Application No. 62/192,819 filed Jul. 15, 2015, the disclosure of which is hereby incorporated herein by reference in its entirety for any and all purposes.

STATEMENT REGARDING FEDERALLY SPONSORED RESEARCH OR DEVELOPMENT

Not Applicable.

BACKGROUND

Field of the Invention

The present invention generally relates to a method and device for diagnosis and treatment of arrhythmias. More particularly, the present invention describes a method and device for diagnosis and treatment of arrhythmias using thermography.

Background of the Invention

Atrial fibrillation (AF) is the most common cardiac arrhythmia (type of irregular heartbeat) and the incidence of AF increases with advancing age. Among American adults, the prevalence of AF is between 2.7 million and 6.1 million individuals, and is projected to increase to between 5.6 and 12.1 million by 2050.

Electro-anatomical mapping is a technology that provides information about the electrical activity of the heart in a visual manner. Currently, electro-anatomical mapping is the main method of finding AF triggers during AF ablation procedures. The success rate of AF ablation with assistance of electrical mapping is around 70%, so establishing an alternative method to find the source of arrhythmia in the heart is a great advantage toward improving the success rate of ablation procedures.

Arrhythmias arise from different locations in the heart and attached vessels and finding the exact location from which they are generated can help physicians guide their therapy to ablate those foci using a variety of techniques. Currently, recording of the electrical activities at the surface of the heart chambers is utilized to identify the source of abnormal electrical currents in the heart. This approach is helpful but not perfect, and its effectiveness is far from optimal. There is continuing need and interest to develop a method and device for diagnosis and treatment of arrhythmias.

SUMMARY

Herein disclosed is a method of detecting and identifying the source of abnormal electrical currents in the heart to assist in ablating these currents, comprising the use of contact or non-contact temperature measurement devices. In an embodiment, the source of abnormal electrical activity of the heart and its attached arteries and veins shows as different temperature patterns from normal segments.

Herein disclosed is a method of assisting in ablating abnormal electrical currents in a heart, comprising placing one or more temperature measurement devices in the heart, wherein said devices utilize contact or non-contact temperature measurement schemes; collecting signals from the one or more temperature measurement devices; and detecting and identifying a source of abnormal electrical currents in the heart or a chamber of interest.

In an embodiment, the method further comprises analyzing the temperature of the chamber of interest, and determining regions of low or high temperature by extension metabolic activity.

In an embodiment, the method comprises measuring myocardial temperature using contact measuring devices, comprising placing an array of thermocouples imbedded on a basket in the cardiac chamber. In an embodiment, the thermocouples are placed in contact with the myocardial tissue. In an embodiment, the array of thermocouples comprises or consists of a series of flexible splines. In an embodiment, the splines are extended (low profile) so as to be placed through a sheath to enable percutaneous insertion. In an embodiment, the splines are expanded (high profile) in the chamber so as to assume a generally spherical or oblong geometry. In an embodiment, expanding the splines increases the volume of the array, enabling contact with the endocavitary surface of the chamber. In an embodiment, the method comprises recording the temperatures.

In an embodiment, contact between the thermocouples and the endocavitary surface is confirmed by utilizing piezo-electric technology. In an embodiment, the thermocouples are intimately coupled electrodes (next to or adjacent to and in contact with the tissue) that deliver and sense electrical current, allowing immediate correlation between electrical and thermal profile of a given region, enabling combining both properties for analysis, and allowing confirmation of contact by measurement of pacing thresholds. Lower thresholds are associated with better contact.

In an embodiment, the electrodes emit a current, the bioimpedance of which current (relative to a patch placed on the patient's skin) provides additional information to identify contact. Since electrical impedance is lower in blood than in muscle or other soft tissues, a lower impedance implies the electrode is making poor contact with the tissue of the endocavitary surface and the resultant temperature measurements may be less accurate.

In an embodiment, the electrodes are positioned using an electroanatomic mapping technique, which technique can be magnetic based, impedance based or both. In an embodiment, the electrodes or thermocouples are radiopaque, enabling identification using fluoroscopy.

In an embodiment, non-contact methods include infrared imaging and are able to develop the thermal map of the cardiac tissues. In an embodiment, the temperatures from some or all locations are measured and compared in real-time. In an embodiment, variables measured and analyzed include absolute temperatures (either focal or global measurements) and/or fluctuation of temperatures during arrhythmia (stable temperatures in an electrically chaotic arrhythmia suggest scar or "rotor" tissue).

In an embodiment, thermal activity and electrical activity are correlated in real-time by automatic or visual logic in order to confirm the critical nature of the local tissue. The following two examples are illustrative: (1) a region that demonstrates stable, elevated temperature during chaotic arrhythmia is likely to be a rotor. This conclusion is supported if the electrode recording adjacent to the thermocouple demonstrates regular, rapid activity; or (2) conversely stable, lower temperatures during chaotic arrhythmia is likely to reflect scar tissue. In this case, the adjacent electrode signals demonstrate lower amplitudes and voltage indicative of the absence of viable tissue. Furthermore, in regular arrhythmias (atrial flutter or ventricular tachycardia), standard pacing maneuvers may be performed to further confirm the critical role of the tissue.

In an embodiment, the method comprises delivering ablation energy from any of a plurality of electrodes placed on the basket.

Herein also disclosed is a device insertable into a tissue to detect aberrant electrical activity using temperature measurement. In an embodiment, the device functions by measuring one or more temperature signals and comparing the temperature signals against each other and against other bodily parameters to determine aberrant electrical activity. Other bodily parameters include electrical activity or electrical signals collected from tissue of fibrosis.

Also disclosed herein is a device, comprising a portion insertable into one or more chambers of the heart; one or more temperature sensors mounted onto the device; and circuitry to collect, process, and store a signal. In an embodiment, the circuitry communicates said signal to an external processor. In an embodiment, the circuitry communicates said signal to the external processor via near field communication (NFC) or Bluetooth, but any other existing or future wireless communication technology may be used for such communication. In an embodiment, the device comprises a battery or external power supply. In an embodiment, the device comprises tracking hardware or software or both to determine where each sensor is in relation to the device and provide a reference area to center said device. The reference area includes any cardiac chamber.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a more detailed description of the preferred embodiment of the present invention, reference will now be made to the accompanying drawings, wherein.

DETAILED DESCRIPTION

Figure 1A:
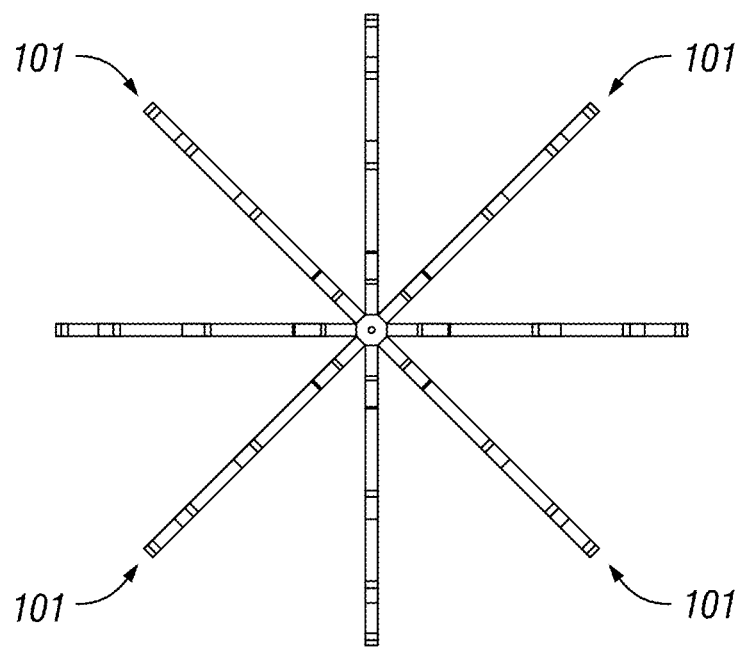
FIGS. 1A-1B illustrate a basket catheter showing proposed location of thermocouples on a standard basket having 8 struts, according to an embodiment of this disclosure.

This disclosure provides a method and apparatus to assist electrophysiologists in the identification of the electrical source of atrial fibrillation (AF) by making a thermoanatomical map of the heart. This method could be used as a complimentary or stand-alone approach to identify arrhythmic sources in the heart. Without wishing to be limited by a theory, we believe that thermoanatomical mapping is a reliable method to identify the electrical rotors and focal impulse sources for AF.

Herein disclosed is a modality, by which points of interest are identified with better accuracy and improved ability to treat such disorders. The method involves detection of temperature using contact and non-contact methods. Examples of clinical applications of the method include but are not limited to atrial fibrillation, atrial flutter, accessory pathways, ventricular fibrillation, and ventricular flutter and other ventricular arrhythmias.

The method and system of this disclosure is able to identify cardiac tissue that serves a critical role in the initiation or maintenance of cardiac arrhythmia. The underlying substrate leading to the tissues critical role is diverse and not necessarily a result of the same pathophysiological process. As an example, two specific mechanisms are described by which tissue temperature plays a critical role in initiation and maintenance of cardiac arrhythmia. For illustrative purposes, they are referred to as the "hurricane" and "tornado" models. In the "hurricane model" the central zone around which the arrhythmic anchors itself is metabolically and electrically quiescent (scar tissue). In the tornado model the "driver" or "rotor" of the arrhythmia is highly active. This activity is more regular and rapid than the surrounding tissue. It should be noted that these mechanisms overlap in terms of their contribution to cardiac arrhythmia. Conversely the same arrhythmia may involve both models.

We shall start with a description of the "hurricane" model: In atrial fibrillation or atrial flutter initiation or sustenance of rotors may be caused by areas of scar tissue. The same applies in some forms of ventricular tachycardia. In these cases the mechanism of tachycardia is referred to as "reentry." In re-entry the arrhythmia circuit anchors itself around the scar tissue. Thus the central anchor is metabolically and/or electrically quiescent (the "eye" of the hurricane). Identification and elimination of this scar tissue (by any of a variety of mechanism including thermal or cryoablation) eliminates the anchor, thus removing the nidus for the arrhythmia. Scar tissue is metabolically inactive. It is also known that temperature is in general correlated with level of metabolic activity. Thus scar tissue has a lower temperature than the surrounding tissue.

Given these facts, identification of myocardial tissue temperatures (either during arrhythmia or during normal rhythm) provides powerful information enabling identification of scar tissue responsible for the re-entrant arrhythmia.

Elimination of this scar region then eliminates the substrate for the aforementioned re-entrant arrhythmias.

The next mechanistic model of arrhythmia is the "tornado." As noted above these mechanisms often overlap. Thus atrial fibrillation, atrial flutter, ventricular fibrillation, and ventricular tachycardia can be caused by this mechanism. In this mechanism tissue with rapid electrical firing creates the nidus of the arrhythmia ("eye of the tornado having the highest energy"). We expect a dose-response relation with detecting higher temperatures when there is a higher frequency of electrical activities. The impulse then passively spreads to the rest of the cardiac tissue. If impulse spreads evenly across the tissue, the arrhythmia appear regular. If the impulse's wavefront breaks down (such as "eddy currents" breaking from the main wavefront) the arrhythmia manifest itself as chaotic activation. This is referred to as "fibrillation" and can occur in atrial or ventricular tissue.

Unlike the "hurricane" or "scar mediated" or "re-entrant" arrhythmia described above, the nidus of these arrhythmias (the eye of the tornado) is activating more rapidly and in a more organized manner than any other region in the heart.

Given the rapid, regular activation of the "rotor" (eye of the tornado), its metabolic activity is higher than the surrounding tissue. One consequence of this is that the temperature of this region of tissue is also higher than the surrounding tissue. Once this region is identified it can be eliminated by any of a variety of techniques (including but not limited to thermal or cryoablative techniques).

Note that in the hurricane model the culprit tissue is less metabolically active (and of lower temperature) than surrounding while in the tornado model the culprit tissue is more metabolically active (and of higher temperature). Currently there are no techniques using thermal properties of cardiac tissue as a guide to identification of these culprit regions.

This disclosure describes a method and device for accurately determining myocardial temperature, analyzing the temperature of the chamber of interest, and determining regions of low or high temperature—by extension metabolic activity.

In one embodiment, an array of thermocouples imbedded on a basket is placed in the cardiac chamber. The thermocouples are placed in contact with the myocardial tissue. The array consists of a series of flexible splines. These splines can be extended (low profile) so as to be placed through a sheath (as an example) to enable percutaneous insertion. Once in the chamber the splines are expanded (high profile) so as to assume a spherical or oblong or other geometry. This increases the volume of the array, enabling contact with the endocavitary surface of the chamber. Recordings of the temperatures are then made.

In another embodiment, adequate contact between the thermocouples and the endocavitary surface may be confined by utilizing piezoelectric technology.

In another embodiment, the thermocouples are intimately coupled (next to or adjacent to) electrodes that can deliver and sense electrical current. This then allows immediate correlation between electrical and thermal profile of a given region, enabling combining both properties as an option for the physician. This embodiment also allows confirmation of contact by allowing measurement of pacing thresholds. Lower thresholds are associated with better contact.

In another embodiment, the electrodes emit a current. The bioimpedance of this current (relative to a patch placed on the patient's skin) can provide another piece of information to identify contact: Since electrical impedance is lower in blood than in muscle or other soft tissues a lower impedance implies the electrode is making poor contact with the tissue and the resultant temperature measurements may be less accurate.

In another embodiment, the electrodes may be located using any of a variety of electroanatomic mapping technologies (magnetic and/or impedance based) available.

In another embodiment, a plurality of the electrodes or thermocouples can be radiopaque. This enables identification using fluoroscopy.

In another embodiment, non-contact methods such as infrared imaging are used to develop the thermal map of the cardiac tissues. The temperatures from some or all locations are measured and compared in real-time. Variables that can be measured and analyzed include but are not limited to absolute temperatures (either focal or global measurements), fluctuation of temperatures during arrhythmia (stable temperatures in an electrically chaotic arrhythmia suggest scar or "rotor" tissue).

In another embodiment, the thermal and electrical activity may be correlated in real-time by automatic or visual logic in order to confirm the critical nature of the local tissue. The following two examples are illustrative: A region that demonstrates stable, elevated temperature during chaotic arrhythmia is likely to be a rotor. This conclusion is supported if the electrode recording adjacent to the thermocouple demonstrates regular, rapid activity. Conversely stable, lower temperatures during chaotic arrhythmia are likely to reflect scar tissue. In this case, the adjacent electrode signals demonstrate lower amplitudes and voltage indicative of the absence of viable tissue. Furthermore, in regular arrhythmias (atrial flutter or ventricular tachycardia) standard pacing maneuvers (well defined in the literature and familiar to any individual versed in the art) may be performed to further confirm the critical role of the tissue.

In another embodiment, ablation energy is delivered from any of a plurality of electrodes placed on the basket.

In various embodiments, the thermal signature is correlated to electric signature because each of the thermocouples is able to both collect temperature signal and to detect electrical activity. As such, the device of this disclosure is able to correlate local thermal patterns with local electrical profiles.

In an embodiment, targets (areas that are to be ablated) include coolest regions and warmest regions in the cardiac tissue. In an embodiment, targets also include areas that have the lowest variability of temperature (regardless of absolute values of the temperature). Such targets are identified by performing a running measurement of temperature in real time to assess which areas have the lowest variability of temperature (regardless of absolute values of the temperature), which indicates that these areas are of interest as they are "regular" during irregular rhythm and thus may be the "eye of a hurricane" (if consistently cold) or the "eye of a tornado" (if consistently warm).

Herein also disclosed is a device insertable into a tissue to detect aberrant electrical activity using temperature measurement. In an embodiment, the device functions by measuring one or more temperature signals and comparing the temperature signals against each other and against other bodily parameters to determine aberrant electrical activity. Other bodily parameters include electrical activity or electrical signals collected from tissue of fibrosis.

Also disclosed herein is a device, comprising a portion insertable into one or more chambers of the heart; one or more temperature sensors mounted onto the device; and circuitry to collect, process, and store a signal. In an embodiment, the circuitry communicates said signal to an external processor. In an embodiment, the circuitry communicates said signal to the external processor via near field communication (NFC) or Bluetooth. In an embodiment, the device comprises a battery or external power supply. In an embodiment, the device comprises tracking hardware or software or both to determine where each sensor is in relation to the device and provide a reference area to center said device. The reference area includes any cardiac chamber.

Advantages.

So far, finding the source of the abnormal electrical current in the heart has been focused on detection of such electrical currents in the heart. Thermography has not been used before for this purpose. (Thermography has been used to detect inflammation in coronary arteries however it has not been previously used for detection of arrythmogenic foci in the heart.)

Existing techniques aim at measuring electrical activity to identify sources of arrhythmias, which are inaccurate and lead to reduced efficacy rate. The method and device of this disclosure utilizes the addition of thermal mapping to currently-available information so that accuracy of diagnosis is increased significantly and treatment efficacy/effectiveness is also improved.

Temperature measurements are performed to identify cardiac tissue that serves a critical role in the initiation or maintenance of cardiac arrhythmia, which consequently improve the ability to detect and treat cardiac arrhythmias.

Figure 1B:
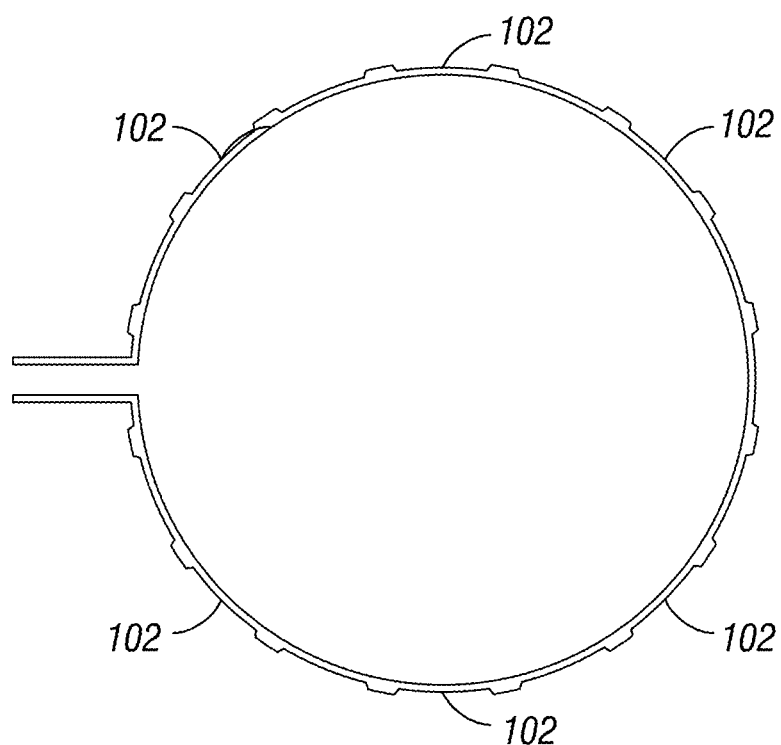

FIGS. 1A-1B illustrate a basket catheter showing proposed location of thermocouples on a standard basket having 8 struts according to an embodiment of this disclosure. As shown, 4 of the 8 struts have measurement capabilities (FIG. 1A). Each of these 4 struts has 3 thermocouples attached to them (FIG. 1B). In FIG. 1A, 101 represents thermocouples on each respective strut. In FIG. 1B, 102 represents thermocouples (with eight electrodes per side, 16 electrodes total as shown).

FIGS. 1C and 1E-1H show a prototype basket catheter according to an embodiment of this disclosure. The basket is fully "deployed" with 4 of the 8 struts having 3 thermocouples on them each. The device has the wires going back to the handle of the basket catheter to allow for percutaneous insertion.

The compressed basket dimensions: 0.210 inches. The deployment tube dimensions are 0.230 inches in outer diameter and 0.210 inches in inner diameter. In an embodiment, using deployment tube, an 18 French sheath would is used to deploy existing device. The wire dimensions are 44 gauge thermocouple wire (0.0020 inches). The thermocouple used is Type T thermocouple. The catheter is tested and all wires are continuous and all readings are within 0.5 degrees of standard thermocouple for accuracy.

Example

We hypothesize that arrhythmic sources in the heart may have a different temperature than the surrounding tissue, and that these differences may be used to identify these regions. In this animal study, the heart rate of sheep is increased by an implanted or external pacemaker. Then the animal undergoes heart catheterization. The trigger points of AF are found by electroanatomical mapping of the atria with the CARTOSOUND system and the temperature of these points and other points inside the heart are recorded using a thermography basket catheter for comparison. We expect this study to document the effectiveness of thermoanatomical mapping during AF ablation to find the AF triggers, which greatly facilitates finding the trigger points (as a complimentary method with electrical mapping or stand-alone method) and may improve the success of this AF ablation procedure.

Atrial fibrillation (AF) is characterized by the disorganized, irregular, and rapid beating of the atria. AF, the most common cardiac arrhythmia, occurs in 1% to 2% of the general population, and its incidence increases with age. 1 In the United States, the prevalence of atrial fibrillation is between 2.7 million and 6.1 million, a number projected to increase to between 5.6 and 12.1 million by 2050.2 The standard therapy for symptomatic AF, which is refractory or intolerant to at least one class 1 or class 3 antiarrhythmic medication, is radiofrequency catheter ablation of the pulmonary veins (PVs). AF is a major risk factor for stroke, independently increasing stroke risk about 4-5 times. Risk of AF-related stroke is almost the same in different types of AF, with an annual rate of 5%, and AF is responsible for at least 15% of all strokes in the United States. AF-related strokes are often severe and patients have increased possibility of permanent disability needing institutional care, and greater short-term and long-term mortality compared with strokes not related to AF. A recent national survey estimated that direct medical costs were 73% higher in patients with AF compared with matched control subjects, representing a net incremental cost of $8705 per patient per year and a national incremental cost between $6.0 and $26.0 billion (2008 US dollars [USD]).

Identifying Rapidly Firing Foci that Drive the Atria.

Atrial fibrillation is characterized by ostensibly disorganized, chaotic atrial electrical and mechanical activity and an accompanying irregular ventricular response. Atrial fibrillation development requires a trigger that finds a susceptible substrate. The pulmonary veins are the most common source of the rapid ectopic beats that trigger AF. We believe that that human AF is sustained by localized sources (electrical rotors and focal impulses), whose elimination (focal impulse and rotor modulation [FIRM]) may improve outcome from AF ablation. This is analogous to the "eye" of the hurricane. The method and apparatus of this disclosure is able to rapidly define this "eye" of the hurricane.

Potential Role for Thermography.

We believe that inflamed atherosclerotic plaques are warmer than adjacent tissue and, furthermore, that their surface temperature correlates with an increased number of macrophages and decreased fibrous-cap thickness. Multiple animal and human experiments have shown that temperature heterogeneity correlates with arterial inflammation in vivo. As such, thermography can be used for detection of vulnerable plaques.

We hypothesize that, because of their higher metabolic rates, rotors acting as the "eye"' of the hurricane of chaotic cardiac activity during atrial fibrillation have a higher local temperature.

Preliminary Studies.

Figure 1C:
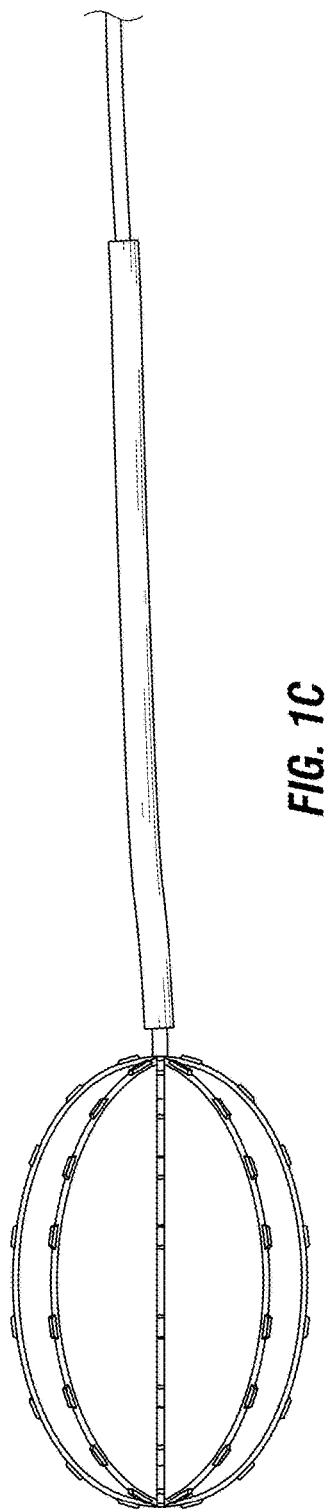
FIGS. 1C and 1E-1H show a prototype basket catheter, according to an embodiment of this disclosure.
Figure 1D:
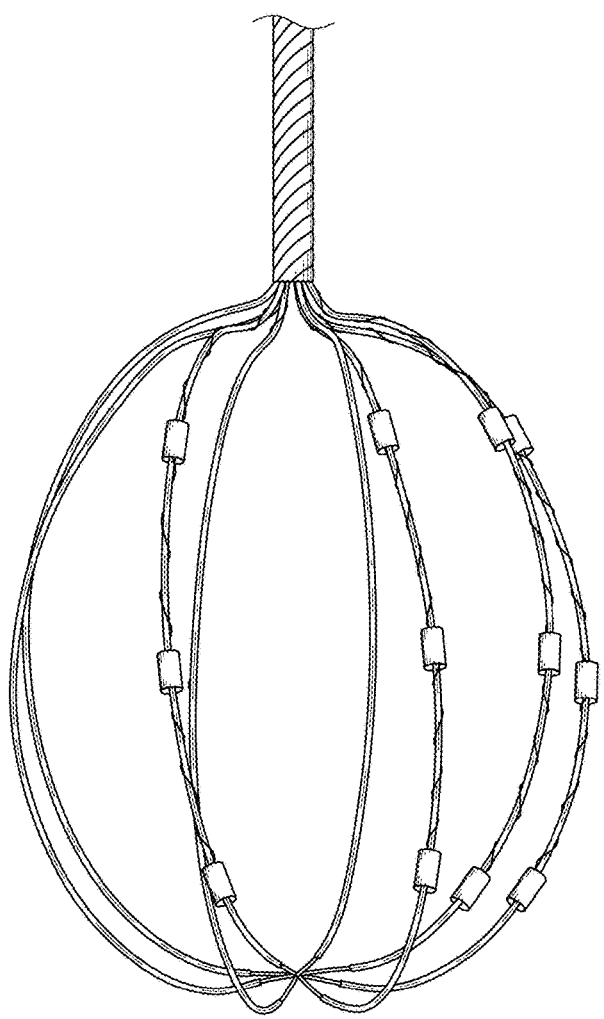
FIG. 1D shows another prototype basket catheter, according to an embodiment of this disclosure.
Figure 1E:
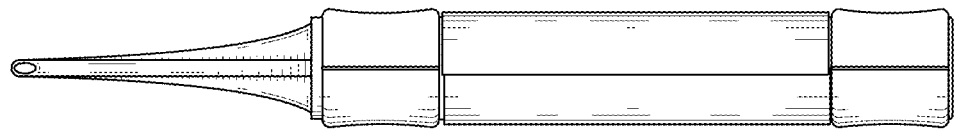
Figure 1F:
Figure 1F:
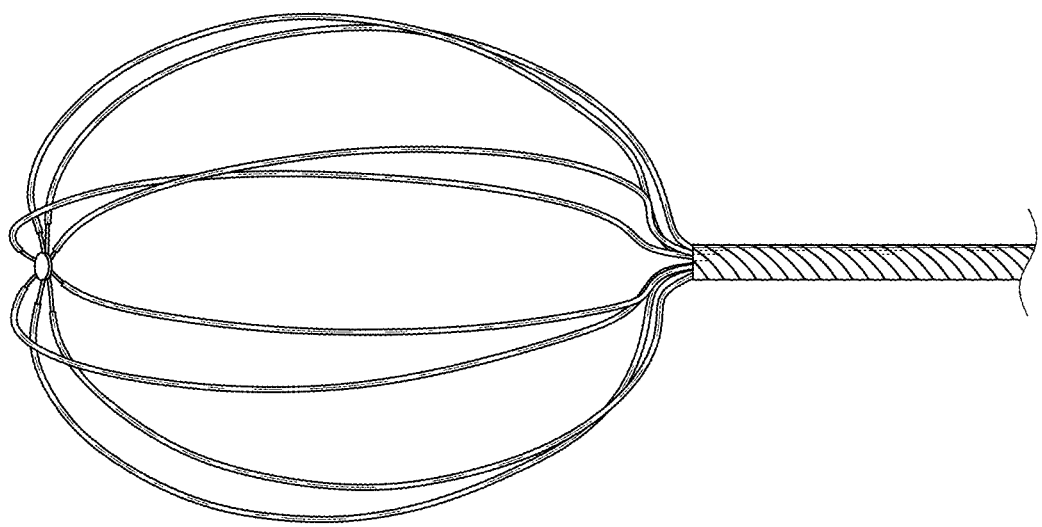
Figure 1G:
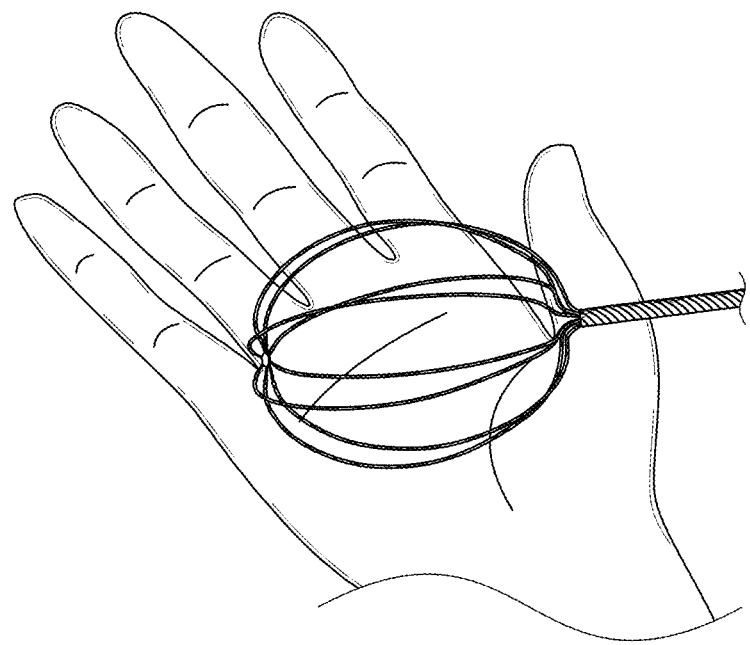
Figure 1H:
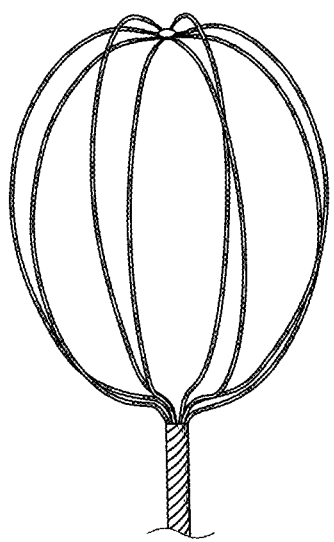
Figure 2:
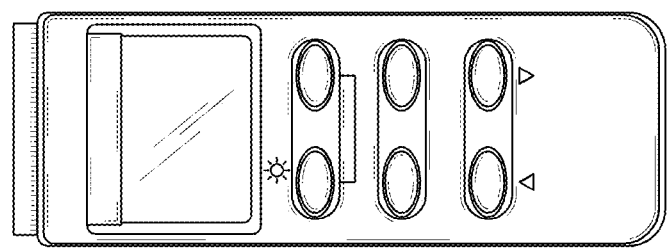
FIG. 2 shows a temperature measurement device used to record temperature from different basket leads, according an embodiment of this disclosure.
Figure 2:
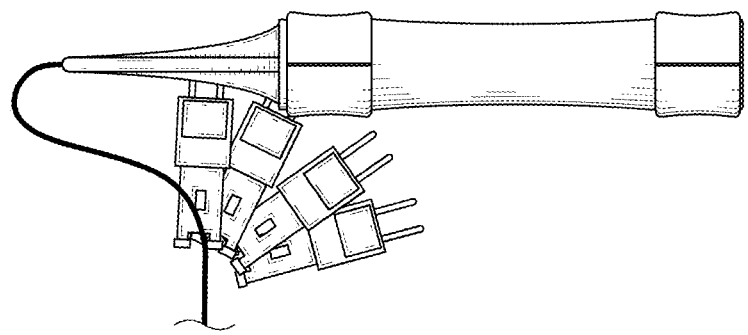
Figure 3:
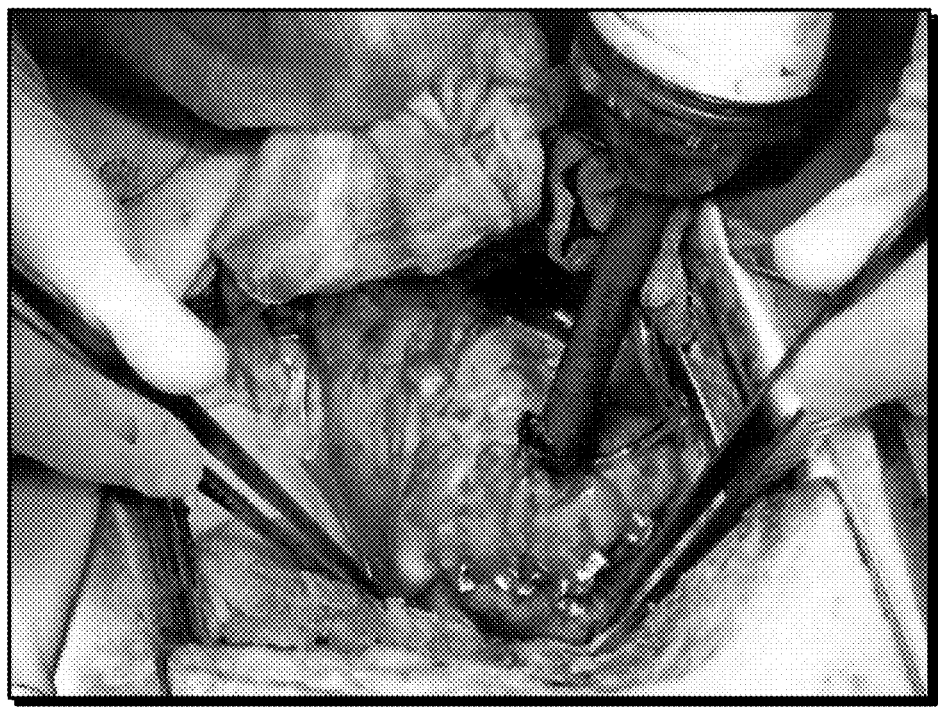
FIG. 3 illustrates a sheep's exposed heart, showing the insertion site of an embodiment of the basket catheter into the atrium.
Figure 4:
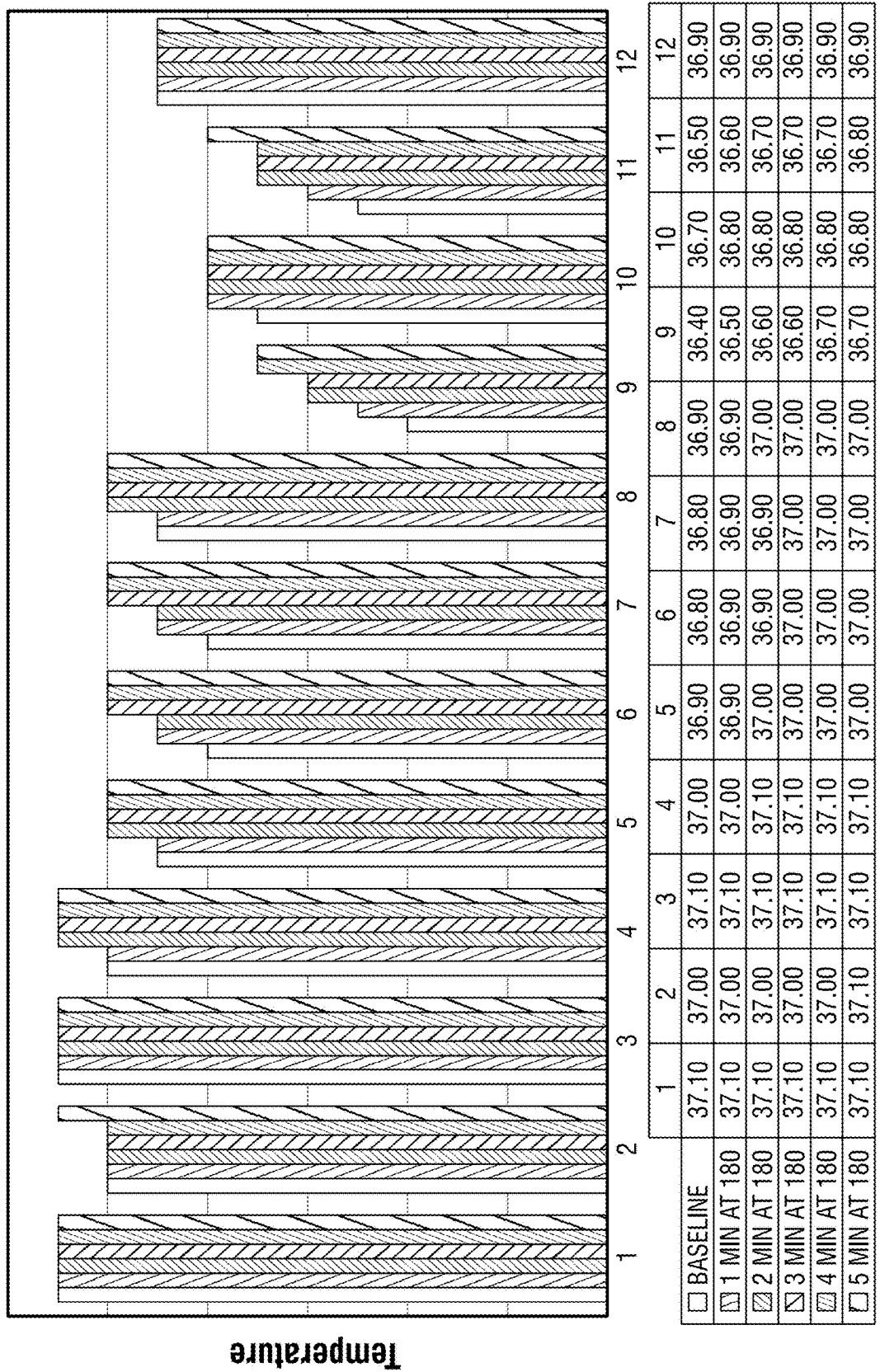
FIG. 4 illustrates increasing temperature after 1, 2, 3, 4 and 5 minutes in certain leads (those in contact with the wall) after induction of tachycardia, after pacing the heart at fast rhythm (180 BPM). The Y axis depicts temperature and the X axis shows each of the 12 leads. Different patterns in column show minutes 1, 2, 3, 4, and 5 after induction of tachycardia.
Figure 5:
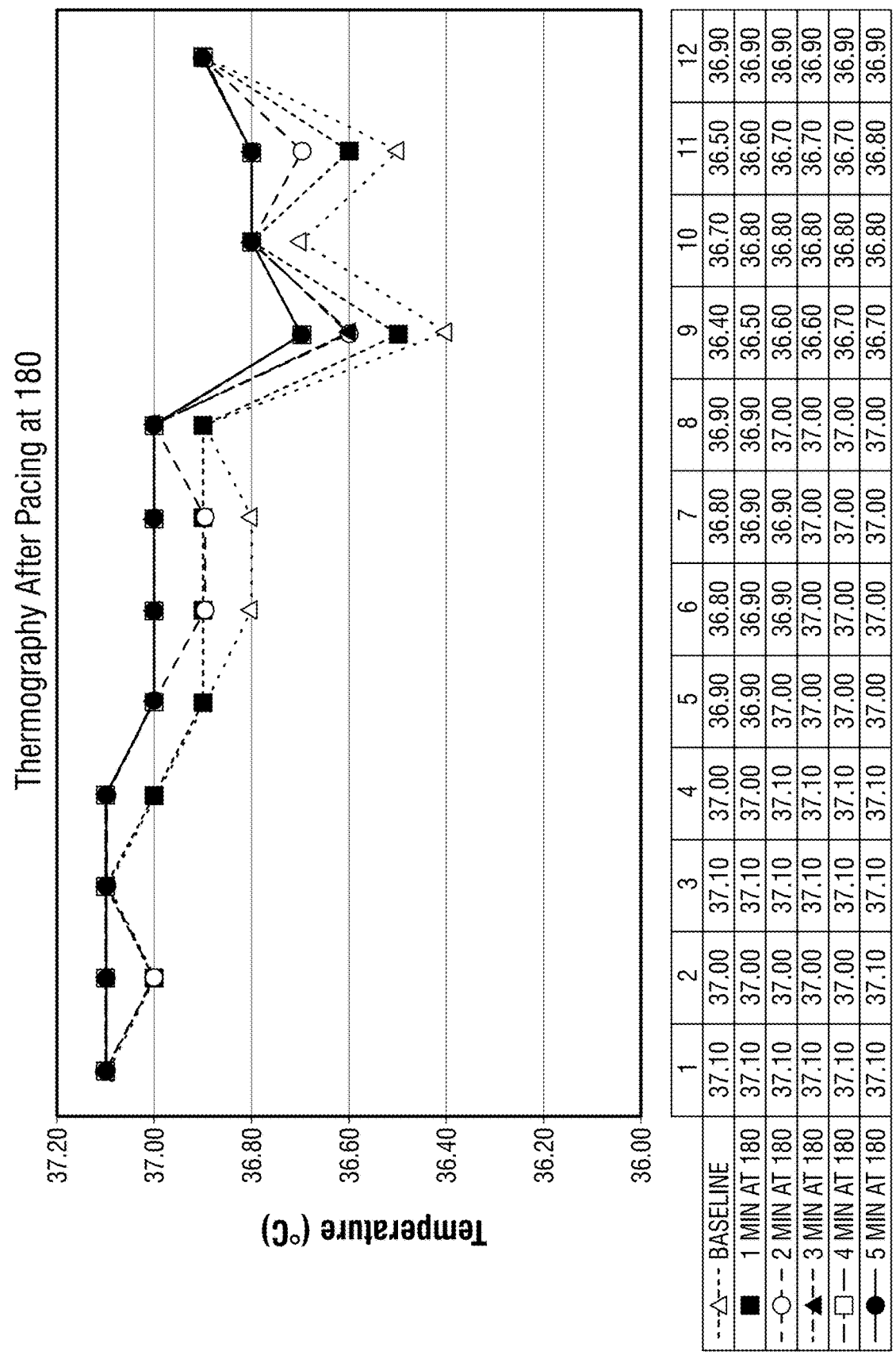
FIG. 5 illustrates after pacing the heart at fast rhythm (180 BPM) and increasing temperature after 1, 2, 3, 4 and 5 minutes in certain leads (right side of the graph, those in contact with the wall) after induction of tachycardia. The Y axis depicts temperature and the X axis shows each of the 12 leads. Different lines show temperature at minutes 1, 2, 3, 4, and 5 after induction of tachycardia.

We constructed our initial thermography basket catheter prototype (Prototype I) by adding 12 thermocouples to an 8-array basket catheter (FIGS. 1D and 2). The thermo basket catheter was placed directly in the left atrium of a sheep through open-heart surgery (FIG. 3). The heart was paced with an external pacemaker at a rate of 180 BPM and the temperature was recorded at baseline and at 1-minute intervals up to 5 minutes along each array. The preliminary data to date has demonstrated that a basket thermocouple placed in the left atrium (location of most AF) can detect not only increased temperatures during increased heart rate, but can also do so in a spatiotemporally accurate manner. The temperature increased significantly after pacing the heart to 180 BPM and in correlation with the length of tachycardia (FIG. 4). Our preliminary data suggests that thermal changes may offer a clue to the "drivers" of AF which has the fastest firing rate. We expect this pilot study to demonstrate the effectiveness of thermoanatomical mapping during AF ablation to locate/identify AF triggers and that this approach is a great help in finding the trigger points (as a complimentary method with electrical mapping or stand-alone method). A thermoanatomical mapping technology may improve the efficacy of this AF ablation procedure. No previous animal or clinical studies have been conducted that use thermoanatomical mapping as a method for finding the electrical source of atrial fibrillation. This study is the first to evaluate the potential role of thermoanatomical mapping in finding the electrical source of atrial fibrillation.

Study Design. The animal study is to determine if thermoanatomical mapping can identify the electrical rotors and focal impulse sources of AF. This study utilizes a sheep model of AF. One set of experiments utilize sheep undergoing short-term, external pacing. Thermoanatomical mapping are made by intra cardiac thermography catheter. We compare the temperature of trigger points which are found by electroanatomical mapping with the myocardial segments adjacent to them to evaluate the effectiveness of using thermoanatomical mapping to find the AF triggers.

Group a (Short-Term Pacing Study, 1 Sheep):
1) Sheep arrives at THI from approved vendor and are held for a minimum of 14 days of quarantine and acclimation prior to use in a study.
2) The study animal is sedated and anesthetized according to study protocol. The animal is then transported to the operating room and placed in the dorsal recumbency position for the final procedure (thermography basket catheter experiment).
3) The animal is paced with external pacemaker at 140, 160, 180, and 200 (BPM) and the heart temperature is recorded at baseline and 1-minute intervals up to 5 minutes.
4) Both femoral veins are accessed using the Seldinger technique. A thermography basket catheter is manually guided and then advanced to the heart via the femoral veins.
5) Electrical mapping is obtained by the CartoSound 3D mapping system. The thermoanatomical mapping is made by thermography basket catheter.
6) Once all study objectives are achieved the animal are humanely euthanized.

Prototype II of the thermography basket as shown in FIGS. 1A-C is designed and built to provide an unprecedented level of spatial resolution. It consists of 8 flexible splines, which are designed to sit on the left atrial wall. Each spline has 8 points of contact, 4 of each are currently attached to a thermistor ready to measure temperature. Temperature data from a total of 32 points are collected. The obtained temperature map is overlapped with the electrical activity map to identify the sources of arrhythmias with a higher accuracy than what is currently available to patients.

Method of Data Analysis.

Quantitative data are expressed as the mean+SEM, while nominal data are expressed as a percentage. Categorical variables are analyzed using chi-square test or Fisher's exact test and continuous variables are analyzed using t-test. The relationship between rate of firing (data from CartoSound 3D mapping) and temperature (data from thermo-basket catheter) is assessed by correlation and regression analysis.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 is inclusive and includes, 1, 2, 3, 4, etc. through 10; greater than 0.10 includes any value greater than 0.10, e.g., 0.1001, 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The disclosures of all patents, patent applications, and publications cited herein are hereby incorporated by reference, to the extent they provide exemplary, procedural or other details supplementary to those set forth herein.

What is claimed is:

1. A method of assisting in ablating niduses of abnormal electrical currents in a heart of a patient, comprising:
   placing an array of thermocouples imbedded on a basket in contact with cardiac tissue, wherein the thermocouples are intimately coupled electrodes;
   inducing tachycardia of the heart;
   collecting temperature signals and electrical signals from the thermocouples;
   comparing the temperature signals against each other to identify regions of the cardiac tissue having higher temperatures and regions of the cardiac tissue having lower temperatures compared to surrounding tissue;
   using an automatic or visual logic to confirm whether higher temperature in a region of the cardiac tissue is correlated with a more regular and rapid electrical signal in an adjacent region of the cardiac tissue compared to the surrounding tissue;
   using the automatic or visual logic to confirm whether lower temperatures in a region of the cardiac tissue is correlated with a lower electrical signal in an adjacent location of the cardiac tissue compared to the surrounding tissue;
   detecting nidus locations of rotors in the cardiac tissue based on the correlation between thermal and electrical activity in the cardiac tissue; and
   identifying mechanisms of the rotors in the cardiac tissue based on the correlation between the thermal and electrical activity in the cardiac tissue, wherein the mechanisms or the rotors include one of "reentry" and "fibrillation."

2. The method of claim 1 wherein the array of thermocouples comprises a series of flexible splines.

3. The method of claim 2 wherein the splines are extended (low profile) so as to be placed through a sheath to enable percutaneous insertion.

4. The method of claim 3 wherein the splines are expanded (high profile) in a chamber of the heart so as to assume a spherical or oblong geometry.

5. The method of claim 4 wherein expanding the splines increases a volume of the array, enabling contact of the thermocouples with an endocavitary surface of the chamber.

6. The method of claim 1 further comprising recording the temperatures.

7. The method of claim 1 wherein contact between the thermocouples and an endocavitary surface of a chamber of the heart is confirmed by utilizing piezoelectric technology.

8. The method of claim 1 wherein the intimately coupled electrodes are configured to deliver and sense electrical current for confirmation of contact between the thermocouples and an endocavitary surface of a chamber of the heart by measurement of pacing thresholds.

9. The method of claim 1 wherein the intimately coupled electrodes are configured to emit a current, the for measuring a bioimpedance between the intimately coupled electrodes and a patch placed on the patient's skin to identify contact between the thermocouples and an endocavitary surface of a chamber of the heart.

10. The method of claim 1 further comprising locating the intimately coupled electrodes using an electroanatomic mapping technique, magnetic or impedance based or both.

11. The method of claim 1 wherein the intimately coupled electrodes or thermocouples are radiopaque, the method further comprising using fluoroscopy.

12. The method of claim 1 further comprising performing infrared imaging to develop a thermal map of cardiac tissues.

13. The method of claim 1 wherein the temperature signals from some or all thermocouples are measured and compared in real-time.

14. The method of claim 13 further comprising analyzing absolute temperatures (either focal or global measurements), and fluctuation of temperatures during arrhythmia.

15. The method of claim 1 further comprising delivering ablation energy from any of a plurality of electrodes placed on the basket.

16. A device for assisting in ablating niduses of abnormal electrical currents in cardiac tissue of a patient, comprising:

an array of thermocouples imbedded on a basket, wherein the thermocouples are intimately coupled electrodes, the basket being insertable into one or more chambers of the heart;

circuitry to collect temperature signals and electrical signals from the thermocouples, wherein said circuitry communicates said temperature signals and electrical signals to an external processor;

wherein the external processor is adapted to compare the temperature signals against each other to identify regions of the cardiac tissue having higher temperatures and regions of the cardiac tissue having lower temperatures compared to surrounding tissue;

automatic or visual logic adapted to confirm whether higher temperature in a region of the cardiac tissue is correlated with a more regular and rapid electrical signal in an adjacent region of the cardiac tissue compared to the surrounding tissue;

wherein the automatic or visual logic is further adapted to confirm whether lower temperatures at in a region of the cardiac tissue is correlated with a lower electrical signal in an adjacent location of the cardiac tissue compared to the surrounding tissue.

17. The device of claim 16 wherein said circuitry communicates said temperature signals and electrical signals to the external processor via near field communication (NFC) or Bluetooth.

18. The device of claim 16 further comprising a battery or external power supply.

19. The device of claim 16 further comprising tracking hardware or software or both to determine where each thermocouple is in relation to the device and provide a reference area to center said device.

20. The device of claim 16 wherein the array of thermocouples comprises a series of flexible splines.

21. The device of claim 20 wherein the splines are adapted to be extended (low profile) so as to be placed through a sheath to enable percutaneous insertion.

22. The device of claim 21 wherein the splines are adapted to be expanded (high profile) so as to assume a spherical or oblong geometry.

23. The device of claim 16 wherein the intimately coupled electrodes are configured to deliver and sense electrical current.

24. The device of claim 16 wherein the intimately coupled electrodes or thermocouples are radiopaque.

* * * * *